United States Patent
Bohrmann

(10) Patent No.: US 11,511,654 B2
(45) Date of Patent: Nov. 29, 2022

(54) DEVICE FOR REDUCING KINETOSIS-RELATED DISORDERS OF AN OCCUPANT WHILE IN DRIVING MODE OF A VEHICLE, AND A VEHICLE

(71) Applicant: Daimler AG, Stuttgart (DE)

(72) Inventor: Dominique Bohrmann, Trier (DE)

(73) Assignee: Mercedes-Benz Group AG, Stuttgart (DE)

( * ) Notice: Subject to any disclaimer, the term of this patent is extended or adjusted under 35 U.S.C. 154(b) by 0 days.

(21) Appl. No.: 17/289,936

(22) PCT Filed: Oct. 31, 2019

(86) PCT No.: PCT/EP2019/079782
§ 371 (c)(1),
(2) Date: Apr. 29, 2021

(87) PCT Pub. No.: WO2020/089368
PCT Pub. Date: May 7, 2020

(65) Prior Publication Data
US 2022/0009393 A1    Jan. 13, 2022

(30) Foreign Application Priority Data
Oct. 31, 2018   (DE) ............... 10 2018 008 630.6

(51) Int. Cl.
*B60N 2/879*     (2018.01)
*B60N 2/806*     (2018.01)
(Continued)

(52) U.S. Cl.
CPC ........... *B60N 2/879* (2018.02); *B60N 2/0244* (2013.01); *B60N 2/806* (2018.02); *A61M 21/02* (2013.01); *B60N 2002/026* (2013.01)

(58) Field of Classification Search
CPC ...... B60N 2/879; B60N 2/806; B60N 2/0244; B60N 2002/026; A61M 21/02
See application file for complete search history.

(56) References Cited

U.S. PATENT DOCUMENTS

| 7,232,187 B1 | 6/2007 | Sundararajan et al. |
| 7,267,367 B2 | 9/2007 | Barvosa-Carter et al. |

(Continued)

FOREIGN PATENT DOCUMENTS

| CN | 101472761 A | 7/2009 |
| CN | 201941630 U | 8/2011 |

(Continued)

OTHER PUBLICATIONS

PCT/EP2019/079782, International Search Report (PCT/ISA/210 and PCT/ISA/220) dated Jan. 7, 2020, enclosing Written Opinion of the International Searching Authority (PCT/ISA/237), with partial English translation (Sixteen (16) pages).

(Continued)

*Primary Examiner* — Philip F Gabler
(74) *Attorney, Agent, or Firm* — Crowell & Moring LLP

(57) ABSTRACT

A device for reducing a kinetosis-related disorder in a driving mode of a vehicle includes a vehicle seat with a headrest and an actuator system. The vehicle seat and/or the headrest is adjustable by the actuator system to position the headrest relative to a head of an occupant on the vehicle seat. A support region of the headrest includes a material which is elastically switchable and the material is solidifiable when a pressure is exerted on the material such that the material stiffens when the head of the occupant sinks into the support region.

8 Claims, 2 Drawing Sheets

(51) Int. Cl.
*B60N 2/02* (2006.01)
*A61M 21/02* (2006.01)

(56) References Cited

U.S. PATENT DOCUMENTS

| | | | | |
|---|---|---|---|---|
| 7,448,678 | B2 * | 11/2008 | Browne | B60N 2/806 |
| | | | | 297/216.12 |
| 7,594,697 | B2 * | 9/2009 | Browne | B60N 2/885 |
| | | | | 297/216.12 |
| 7,758,121 | B2 * | 7/2010 | Browne | B60R 7/043 |
| | | | | 297/452.41 |
| 7,857,381 | B2 | 12/2010 | Humer et al. | |
| 8,857,904 | B2 | 10/2014 | Gaeng et al. | |
| 9,238,427 | B2 * | 1/2016 | Baumgarten | B60N 2/806 |
| 9,596,894 | B2 * | 3/2017 | Carlson | A41D 13/015 |
| 2006/0125297 | A1 * | 6/2006 | Orizaris | B60N 2/838 |
| | | | | 297/216.12 |
| 2018/0147474 | A1 * | 5/2018 | Hodge | A63B 71/1291 |

FOREIGN PATENT DOCUMENTS

| | | |
|---|---|---|
| CN | 103419689 A | 12/2013 |
| DE | 195 09 014 A1 | 9/1996 |
| DE | 10 2005 014 549 A1 | 10/2005 |
| DE | 11 2007 000 947 B4 | 2/2009 |
| DE | 10 2009 033 719 A1 | 3/2010 |
| DE | 10 2010 054 651 A1 | 6/2012 |
| DE | 10 2011 016 959 A1 | 10/2012 |
| DE | 10 2014 224 835 A1 | 6/2016 |
| EP | 1 806 257 B1 | 7/2007 |
| EP | 3 275 726 A1 | 1/2018 |
| TW | M511444 U | 11/2015 |

OTHER PUBLICATIONS

German-language German Office Action issued in German application No. 10 2018 008 630.6 dated Apr. 15, 2019 (Six (6) pages).
Chinese Office Action issued in Chinese application No. 201980071696.8 dated Aug. 15, 2022, with partial English translation (ten (10) pages).

* cited by examiner

DEVICE FOR REDUCING KINETOSIS-RELATED DISORDERS OF AN OCCUPANT WHILE IN DRIVING MODE OF A VEHICLE, AND A VEHICLE

BACKGROUND AND SUMMARY OF THE INVENTION

The invention relates to a device for reducing kinetosis-related disorders of an occupant while in driving mode of a vehicle having a vehicle seat and a headrest. In addition, the invention relates to a vehicle having such a device.

A headrest of a motor vehicle is known from EP 1 806 257 B1. The headrest comprises a support cushion which comprises a headrest part and a secondary part, which is adjacent at least to the lower edge of the head support part, wherein the front surfaces of the headrest part and the secondary part are in mutual extension in the free state. The headrest part has a softness greater than that of the secondary part, such that by supporting the head of an occupant, the headrest part is depressed to a depth sufficient to cause the secondary part to protrude with respect to the headrest part, such that this forms a neck support.

Further headrests for vehicles are described in DE 195 09 014 A1, DE 10 2011 016 959 A1, DE 10 2010 054 651 A1 and DE 10 2005 014 549 A1.

The object of the invention is to specify a device which is improved with respect to the prior art for reducing kinetosis-related disorders of an occupant of a vehicle in driving mode, and a vehicle having such a device.

A device for reducing kinetosis-related disorders while in driving mode of a vehicle having a vehicle seat and a headrest comprises an actuator system for adjusting the vehicle seat and/or the headrest, at least in sections, for positioning the headrest relative to the head of an occupant on the vehicle seat. The adjustment can take place in several degrees of freedom, rotationally and translationally.

By means of a device designed in this way, the head in particular is positioned in comparatively good contact with the headrest, such that head acceleration can be substantially reduced during driving, in particular during autonomous driving. This, in turn, can largely eliminate the occurrence of kinetosis-related disorders of the occupant. The head is thus stabilized.

Kinetosis, or motion sickness, is characterised in particular by symptoms such as fatigue, lack of focus, dizziness, paleness, headaches, sweating and/or nausea.

For optimized positioning of the occupant's head relative to the headrest, a support area of the headrest comprises a material which can be elastically switched. The switching can be activated manually by pressing a button, by voice input or automatically. If the head sinks into the support area, the material solidifies such that the head is stabilized in its position. The material in the support area solidifies when the head in particular exerts pressure on the support area. The head thus sinks into the support area, the material solidifies and the head is stabilized in its position relative to the headrest.

In one embodiment, metal threads are integrated into the material to generate a magnetic field to solidify the material. When the magnetic field is generated, the material solidifies to stabilize the head relative to the headrest.

Another embodiment provides that, when an electrical voltage is applied, the material solidifies such that that occupant's head is stabilized in its position.

In another embodiment, the material chemically and reversibly solidifies, whereby the occupant's head is stabilized in position, such that kinetosis-related disorders of the occupant can at least be reduced.

One embodiment of the device provides that the support area is surrounded, at least in sections, by a rigid structure. This rigid structure substantially predetermines the shape of the headrest and defines an extent of the support area.

In order to optimize the stabilization of the head, at least one actuator designed as a pincer element is arranged in the area of the rigid structure, the free end of which projects into the support area of the headrest when the actuator is activated. In the state of the head sunk into the support area, the pincer element is positioned laterally relative to the head in such a way that the stabilization of the head is increased.

Furthermore, to optimize the contact of the head with the support area of the headrest, a movable support element is integrated in a seat back of the vehicle seat in the direction of the occupant. When the support element is extended, a hyperextension of the occupant's body, in particular of the upper body, is achieved such that the head is always in contact with the headrest while the vehicle is in driving mode. The support element is a similar component to the so-called lumbar support.

Furthermore, the invention relates to a vehicle having such a device for reducing kinetosis-related disorders of the occupant in the driving mode of the vehicle.

Exemplary embodiments of the invention are explained in more detail below using drawings.

DETAILED DESCRIPTION OF THE DRAWINGS

Figure 1:
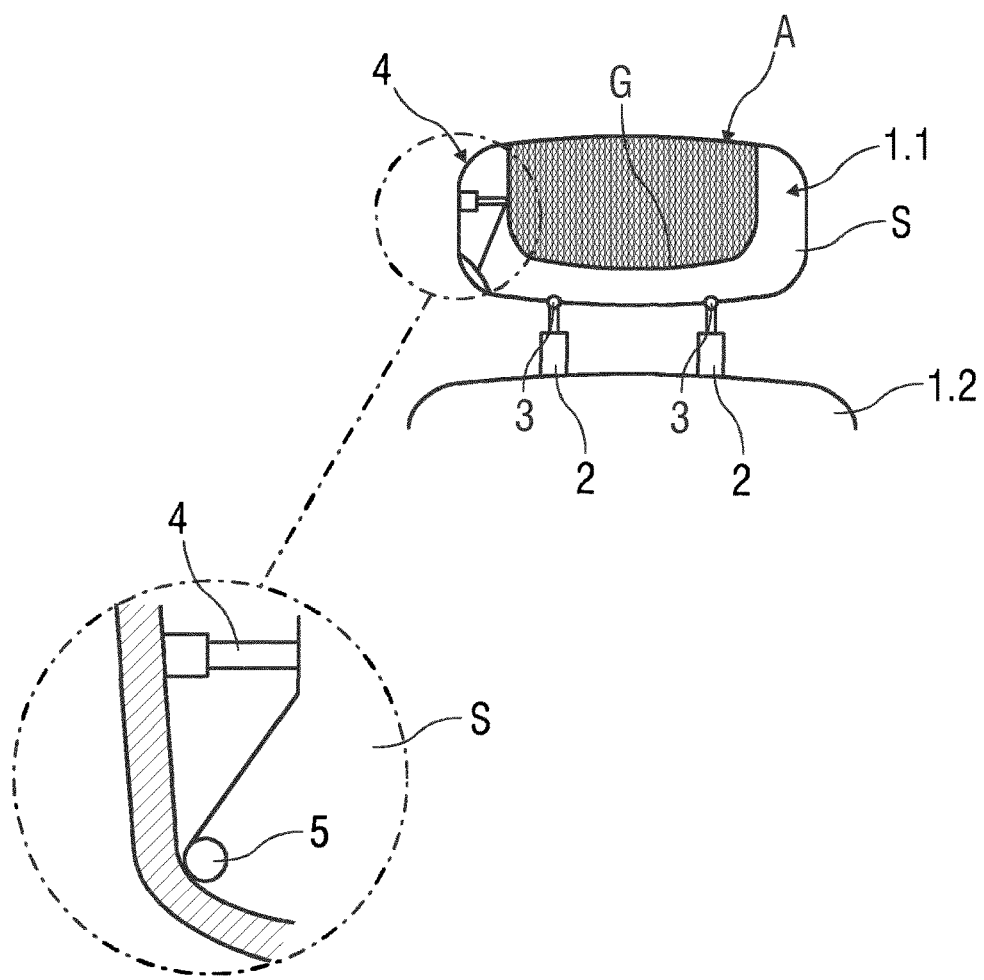
FIG. 1 schematically, shows a sectional depiction of a front view of a headrest of a device for reducing kinetosis-related disorders of an occupant in the driving mode of a vehicle and an enlarged section of the headrest in the region of an actuator, FIG. 2 schematically, shows a vehicle seat in an upright position, FIG. 3 schematically, shows the vehicle seat in a position pivoted around a vehicle transverse axis, FIG. 4 schematically, shows an automatically movable headrest, and FIG. 5 schematically, shows a section of a sectional depiction of a seat back of the vehicle seat in the area of a movable support element.

Parts corresponding to one another are provided with the same reference numerals in all figures.

Figure 2:
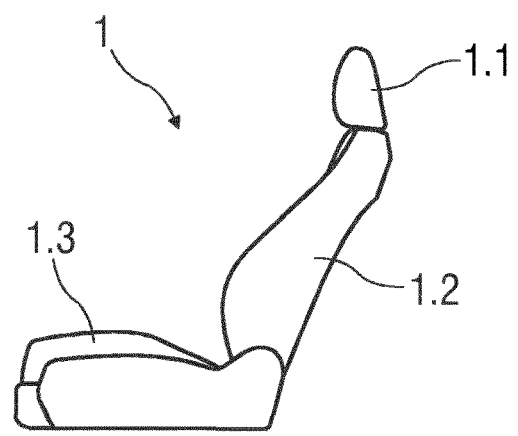
Figure 3:
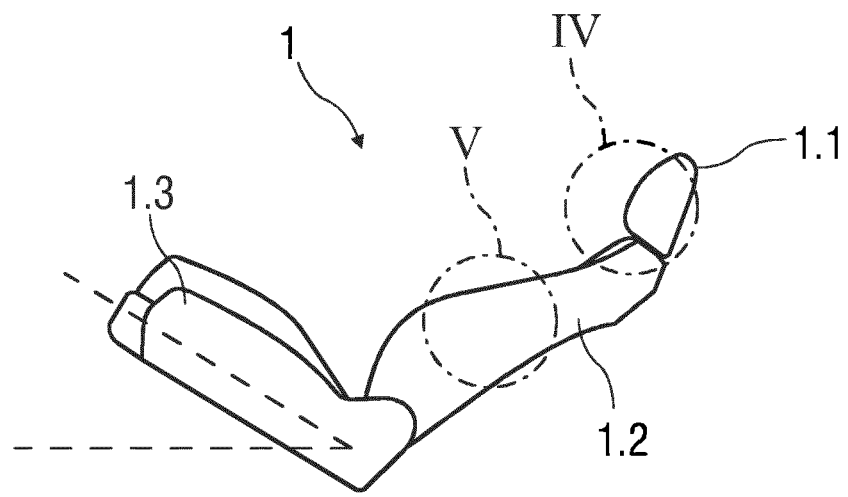

FIG. 1 shows a sectional depiction of a front view of a headrest 1.1 of a vehicle seat 1 shown in FIGS. 2 and 3, which also comprises a seat back 1.2 and a seat cushion 1.3 forming a seat surface. In addition, an enlarged section of the sectional depiction is depicted in FIG. 2.

The vehicle seat 1 is a component of a device for reducing kinetosis-related disorders of an occupant, who is not shown, in the driving mode of a vehicle which is also not shown.

If the occupant is a vehicle user, i.e., a driver of the vehicle, and the vehicle has an assistance system for autonomous driving operation, the occupant can engage in other activities during autonomous driving operation. By way of example, the occupant can read a book or watch a film while the vehicle is driving to its destination.

Since the occupant, who may be a passenger or another occupant of the vehicle, is distracted from the driving action and is concentrating on the other activity, there is a risk of kinetosis, or motion sickness, occurring.

Kinetosis can also occur in a front passenger or other occupant in the rear of the vehicle if the vehicle does not have the assistance system for autonomous driving.

Kinetosis refers to physical reactions such as paleness, headaches, nausea, vomiting and dizziness, which are triggered in an occupant by an unfamiliar movement, particularly in a vehicle. The physical reactions are referred to as kinetosis-related disorders or symptoms.

In order to at least substantially reduce the risk of kinetosis-related disorders occurring, the device described below is provided.

In particular, the device serves to stabilise a head and also a body of the occupant on the vehicle seat 1 at least to reduce the kinetosis-related disorders.

The headrest 1.1 comprises a support region A arranged on a side of the headrest 1.1 facing the occupant, wherein the support region A is surrounded, at least in sections, by a rigid structure S formed in particular from hard plastic, for example from at least one thermoplastic and/or from at least one thermoset.

A gel G and/or a shaping layer are/is present between the support region A and the rigid structure S.

The support region A is formed from a material, in particular from an elastically switchable foam. This means that the material stiffens when the head sinks into the support region A. The material thus has individual hardness properties, wherein the material has a higher hardness when the occupant's head is firmly applied to the support region A.

An activation for switching the material, in particular the foam, can be performed manually by means of a button press, by means of a voice input and/or automatically.

In order to solidify the material of the support region A, metal threads can be integrated into the material, by means of which a magnetic field can be built up to solidify the material.

Alternatively or additionally, the material solidifies if an electric voltage is applied, wherein again alternatively or additionally, it can be provided that the material solidifies when pressure is applied to it.

A further alternative or additional possibility is represented by a chemical and reversible solidification of the material in order to stabilise the head in the state in which it is sunk into the support region A.

According to the present exemplary embodiment, the headrest 1.1 is attached to the seat back 1.2 by means of actuators 2, such that the headrest 1.1 is movable in the direction of the vehicle longitudinal axis. In particular, the headrest 1.1 is moved in the direction of the occupant such that the head rests against the support region A. In particular, the headrest 1.1 is arranged on the respective actuator 2 by means of a ball bearing. The ball bearings serve to compensate for at least rotational movements.

A vibration motor 3 is arranged on the headrest 1.1 in the area of the respective actuator 2; these can be activated in order to introduce vibrations into the head of the occupant, such that in particular the equilibrium organ of the occupant is desensitised and thus the kinetosis-related disorders are reduced.

A pincer element 4 is arranged laterally in the headrest 1.1 as a further actuator, which is operatively connected to a spring element 5, wherein the spring element 5 is pretensioned in an initial position of the pincer element 4. In the activated state, a free end of the pincer element 4 projects into the support region A of the headrest 1.1, as a result of which the occupant's head is additionally stabilized in its position on the headrest 1.1.

Figures 4, 5:

To optimize the contact of the head with the support region A, the headrest 1.1 can be moved in the direction of the head such that the head can be moved forwards, as shown in more detail in FIG. 4. The set-up angle and extension path of the headrest 1.1, and thus the position and orientation of the head, are determined by the user's wishes. In a resting phase, the headrest 1.1 is retracted such that a flat head position is achieved. During an active activity, such as reading or the desire to have a good view of the outside, the headrest is raised and the angle adjusted. The head thereby straightens up without changing the position of the entire body in the space.

FIG. 2 shows the vehicle seat 1 in its initial position, in which the vehicle seat 1 is positioned substantially upright. FIG. 3 shows the vehicle seat 1 in a position pivoted around a vehicle transverse axis.

The aim is here is for the occupant's head to rest as optimally as possible against the support region A of the headrest 1.1.

To implement and optimize the contact of the head with the headrest 1.1, the upper body of the occupant is deliberately hyperextended. For this purpose, a movable support element, which is not depicted in more detail, is arranged in the seat back 1.2 of the vehicle seat 1 and is positioned in its operative position in the direction of the occupant, as shown in FIG. 5. The support element is designed in a similar way to a lumbar support.

In the operative position of the support element, it moves perpendicularly to the seat back 1.2 from the latter in the direction of the centre of the upper body of the occupant, such that the centre of the upper body moves away and the head of the occupant is thereby positioned in the direction of the headrest 1.1, in particular of the support region A.

Furthermore, it can be provided that a seat belt worn by the occupant is tightened by means of a reversible belt tensioner before the occurrence of a respective acceleration in order to fasten the body of the occupant to the vehicle seat 1 and thereby at least reduce kinetosis.

By means of the device for reducing kinetosis-related disorders of the occupant during driving mode of the vehicle, the head as well as the body of the occupant can be stabilized in its position. In addition, the equilibrium organ can be aligned and the autonomic nervous system can be influenced.

Furthermore, the device makes it possible to define a working and relaxation position for carrying out activities not related to driving.

The invention claimed is:

1. A device for reducing a kinetosis-related disorder in an autonomous driving mode of a vehicle, comprising:
   a vehicle seat with a headrest; and
   an actuator system, wherein the vehicle seat and/or the headrest is adjustable by the actuator system to position the headrest relative to a head of an occupant on the vehicle seat;
   wherein a support region of the headrest comprises a material which is elastically switchable;
   wherein the material is solidifiable when a pressure is exerted on the material such that the material stiffens when the head of the occupant sinks into the support region and such that the stiffened material stabilizes a position of the head of the occupant, when sunk into the support region, relative to the headrest which reduces an acceleration of the head of the occupant and which reduces a risk of kinetosis occurring to the occupant.

2. The device according to claim 1, wherein metal threads are integrated into the material, wherein a magnetic field is generatable by the metal threads, and wherein the material is solidifiable by the magnetic field.

3. The device according to claim 1, wherein the material is solidifiable when an electrical voltage is applied to the material.

4. The device according to claim 1, wherein the material is solidifiable chemically and reversibly.

5. The device according to claim 1, wherein the support region is surrounded, at least in sections, by a rigid structure.

6. The device according to claim 5 further comprising an actuator configured as a pincer element, wherein the actuator is disposed in a region of the rigid structure, and wherein a free end of the actuator projects into the support region in an activated state of the actuator.

7. The device according to claim 1 further comprising a support element which is movable in a direction of the occupant, wherein the support element is integrated into a seat back of the vehicle seat.

8. A vehicle, comprising:
the device according to claim 1.

* * * * *